US006400797B1

(12) United States Patent
D'Amico (10) Patent No.: US 6,400,797 B1
(45) Date of Patent: Jun. 4, 2002

(54) SAMPLE CHANGER FOR CAPILLARY GEOMETRY X-RAY DIFFRACTOMETERS

(76) Inventor: Kevin L. D'Amico, 720 W. Walnut St., Hinsdale, IL (US) 60521

( * ) Notice: Subject to any disclaimer, the term of this patent is extended or adjusted under 35 U.S.C. 154(b) by 50 days.

(21) Appl. No.: 09/602,634

(22) Filed: Jun. 22, 2000

(51) Int. Cl.[7] .............................................. G01N 23/20
(52) U.S. Cl. ....................................... 378/79; 378/208
(58) Field of Search .............................. 378/71, 73, 79, 378/81, 208; 414/222.03, 223.02, 226.05; 206/537, 538, 562

(56) References Cited

U.S. PATENT DOCUMENTS

| | | | |
|---|---|---|---|
| 3,654,460 A | | 4/1972 | Payton et al. ............... 250/51.5 |
| 4,641,329 A | | 2/1987 | Green et al. .................... 378/79 |
| 4,770,593 A | | 9/1988 | Anderson .................... 414/331 |
| 5,127,039 A | * | 6/1992 | Hesch .......................... 378/79 |
| 5,737,385 A | * | 4/1998 | Prevey, III et al. ............ 378/71 |
| 6,111,930 A | * | 8/2000 | Schipper ....................... 378/79 |

OTHER PUBLICATIONS

Beno et al., "Application of New Synchrotron Powder Diffraction Techniques to Anomalous Scattering from Glasses", *Rev. Sci. Instrum.*, 66(2):1308–1310 (Feb. 1995).
Cheetham and Wilkinson, "Synchrotron X–Ray and Neutron Diffraction Studies in Solid–State Chemistry", *Agnew. Chem. Int. Ed. Engl.*, 31:1557–1570 (1992).
Earnest et al., "The Macromolecular Crystallography Facility at the Advanced Light Source", *J. of Crystal Growth*, 168:248–252 (1996).
Kawasaki and Iwasaki, "Rapid Mapping of Texture in Polycrystalline Materials Using an Imaging Plate on a Synchrotron Radiation Source", *J. Synchrotron Rad.*, 2:49–55 (1995).
Creagh et al., "An eight–position capillary sample spinning stage for the diffractometer at BL20B at the Photon Factory", *J. Synchrotron Radiation*, 5:823–825 (1998).
Hodeau et al., Nine crystal multi–analyser stage for high resolution powder diffraction between 6 and 40keV, *SPIE*, 3448:353–361(1998.

* cited by examiner

Primary Examiner—David P. Porta
(74) Attorney, Agent, or Firm—Pennie & Edmonds LLP (57) ABSTRACT

This present invention provides a sample changer for automatically changing from one sample to the next in support of high throughput X-ray powder diffraction data acquisition in a capillary geometry. The samples are mounted on the outer rim of a disk or turntable, with each sample having its capillary axis parallel to a radius emanating from the center of the disk on which the samples are mounted. Each sample is mounted on a separate motor shaft which permits the sample to be rotated about the longitudinal axis of the capillary during data acquisition. To change from one sample to the next, the disk or turntable is rotated about its axis thereby presenting in turn each new sample to a X-ray beam. When the data acquisition is completed for that sample, a new sample is rotated into the beam and its data collection is carried out.

36 Claims, 9 Drawing Sheets

(Prior Art)

FIG. 1

(Prior Art)

SAMPLE CHANGER FOR CAPILLARY GEOMETRY X-RAY DIFFRACTOMETERS

TECHINCAL FIELD

The present invention relates generally to sample changers for X-ray diffractometers, and in particular to an automatic sample changer for use with capillary geometry powder-diffraction systems that permits high-throughput acquisition of X-ray powder patterns.

BACKGROUND OF THE INVENTION

Powder X-ray diffraction techniques are used to measure the structural properties of a wide variety of materials. For a general review of X-ray diffraction, see B. E. Warren, X-ray Diffraction, Dover, 1990. Typically, a beam of X-rays is passed through a sample of randomly-oriented microcrystals to produce a pattern of rings on a distant screen. The pattern correlates with the structure of the molecules comprising the microcrystals.

Powder diffraction may be used for the identification of the structural phases in a sample which may contain multiple structural representations of a material. Powder diffraction may also be used as a means of verifying that a powder sample contains a material whose structure has been determined by a single crystal X-ray diffraction measurement. Typically, a powder X-ray diffraction pattern is calculated for a known material, after which a new measured powder pattern is compared to the known material's pattern which is then used to verify that the sample measured is representative of the expected compound.

The development of synchrotron radiation sources has lead to advancements in powder X-ray diffraction techniques. See, e.g., Synchrotron Radiation Research, H. Winick and S. Doniach, Eds., Plenum, N.Y., (1979); Synchrotron X-ray Powder Diffraction, J. B. Hastings, W. Thomlinson, and D. E. Cox, Journal of Applied Crystallography, 17, 85(1984); and Powder Diffraction, D. E. Cox in G. S. Brown and D. E. Moncton, Eds., Handbook on Synchrotron Radiation, Elsevier, 3, 155 (1991). A synchrotron is a cyclic particle (electron, proton, heavy-ion) accelerator in which a particle is confined to its orbit by a magnetic field that gradually strengthens as the particle's momentum increases. Acceleration is produced by an alternating electric field that is in synchronism with orbital frequency. A consequence of the acceleration is the emission of synchrotron radiation. This radiation is a broad-spectrum (white) emission that resembles the white radiation of an X-ray tube but is immensely more intense (100 to $10^4$ times the intensity of a conventional characteristic line). See, e.g., X-ray Structure Determination—A Practical Guide, pp 14–15, Stout and Jensen, $2^{nd}$ edition, Wiley Interscience (1989).

There are currently several powder X-ray diffraction instruments at synchrotron radiation sources around the world where powder X-ray diffraction is practiced. The most favored geometry for carrying out powder X-ray diffraction at a synchrotron radiation source is high resolution geometry. Typically, a sample is mounted in either a flat plate or capillary geometry and X-ray beams are directed at the sample. X-rays diffracted by the sample are analyzed by an analyzer crystal before being counted by an X-ray detector. Such geometries, where the diffracted beams are analyzed by diffraction, utilize standard commercial powder X-ray diffraction instruments.

The analyzer crystal is typically referred to as a "diffracted beam monochromator" and is typically of a mosaic material such as graphite or lithium fluoride. Owing to the properties of synchrotron radiation, the analyzer crystal of choice for the synchrotron radiation powder diffraction method is a perfect crystal of either silicon or germanium. Such perfect crystal analyzers are typically not used for traditional tube X-ray sources, because the signal rates are too low, (typically being several orders of magnitude lower than those for a synchrotron radiation experiment). The data collection times for traditional tube X-ray sources are also prohibitively long.

High resolution powder X-ray diffraction measurement at a synchrotron radiation source provides numerous advantages over traditional measurement systems using X-ray tubes. In particular, the energy of the X-rays can be freely chosen with a synchrotron radiation source; the angular resolution of this method is far superior to the X-ray tube based technique; it is possible to more accurately determine the positions of the measured diffraction peaks; one can better discriminate against fluorescence from those samples that fluoresce since only a narrow band of energies around the elastically scattered X-rays from the sample are counted, thereby reducing background interference; and background interference from air scatter in the neighborhood of the sample is also reduced. The combination of the above advantages has made powder X-ray diffraction techniques at synchrotron radiation sources a favored technique for complex materials analysis problems. In some cases powder X-ray diffraction data has made it possible to solve unknown structures of materials directly from powder diffraction data. See, e.g., F. Favier, et al., Inorganic Chemistry, 37, 1776–1780 (1998).

As mentioned above, when collecting X-ray powder diffraction data, it is possible to mount the samples in either a flat plate geometry or a capillary geometry. Both geometries have advantages and disadvantages, and it does not hold true that one geometry can be used for all samples. However, the availability of synchrotron radiation sources and the potential for using X-ray energies higher than the traditional molybdenum K-alpha radiation available from X-ray tubes has made the capillary geometry a favored geometry at synchrotron radiation sources for many analysis problems.

In a capillary geometry system, the sample is mounted in a capillary of, for example, 1 millimeter in diameter, and the energy of the X-rays is adjusted to optimally penetrate the thickness of the sample with the proper amount of absorption. In either the flat plate or capillary geometry systems, it is often necessary to rotate or rock the sample during data acquisitior. This is because the samples often do not contain an appropriate statistical representation of all possible orientations, due, for example, to preferred orientation effects, and therefore oscillating them during data acquisition can help to alleviate this problem.

A recent development in the data collection capabilities at synchrotron radiation sources is the use of multi-element detectors to measure powder patterns. See, e.g., J. L. Hodeau, et al., SPIE Proceedings, 3448, 353–361 (1998). In this high-resolution diffraction experiment performed with analyzer crystals, nine analyzer crystals and nine detectors have been mounted in parallel to detect the diffracted X-rays. Such multi-element detectors speed up the data acquisition process considerably, making it possible to rapidly analyze a sample. To further speed up the analysis of samples, it would be desirable to have a sample changer which automatically changes multiple samples mounted in a capillary geometry, while rotating the samples during data acquisition.

U.S. Pat. No. 4,770,593 to Anderson ("Anderson") discloses a changer for a flat plate geometry utilizing a conventional X-ray tube. U.S. Pat. No. 4,641,329 to Green, et al. ("Green et al.") discloses a holder for a capillary geometry sample for a commercial powder X-ray diffraction instrument. These two patents address conventional X-ray diffraction with an X-ray tube source. Anderson-teaches a means for changing samples in an unattended manner in a flat plate geometry, while Green et al. teach the use of a conventional diffractometer with a capillary geometry. Neither patent teaches, nor suggests, an efficient high volume capillary geometry sample changer for use with a synchrotron X-ray source.

Creagh et al. teach a sample changer with multiple independently rotating capillary tubes for use with a synchrotron radiation powder X-ray diffractometer. See, e.g., D. C. Creagh et al., Journal of Synchrotron Radiation, 5, 823–825 (1998). Creagh et al. do not, however, teach a device for holding a vast plurality of samples for extended analysis periods. In fact, the very nature of the device taught by Creagh et al. limits the amount of samples that one can position on the sample changer before inaccuracies and alignment problems come into play. A sample changer which more effectively mounts, changes, rotates, and collects data from a plurality of samples using high resolution geometry at a synchrotron radiation source would therefore be highly desirable.

SUMMARY OF THE INVENTION

This present invention provides a sample changer for automatically changing from one sample to the next in support of high throughput X-ray powder diffraction data acquisition in a capillary geometry. The sample changer of the invention can be used with either a conventional X-ray source or a synchrotron radiation X-ray source, though the latter is preferred for high resolution measurements. During data acquisition, the samples are each rotated about the longitudinal axis of the capillary, which is aligned along the axis of rotation for the scattering angle (typically called two-theta). In a preferred embodiment, the samples are mounted on the outer rim of a disk or turntable, with each sample having its capillary axis parallel to a radius emanating from the center of the disk on which the samples are mounted. Each sample is mounted on a separate motor shaft which permits the sample to be rotated about the longitudinal axis of the capillary during data acquisition. To change from one sample to the next, the disk or turntable is rotated about its axis thereby presenting in turn each new sample to the beam. The sample changer may include switching means which begin the sample rotating about the longitudinal axis of the capillary just prior to, or concurrent with, the sample being exposed to the X-ray beam. When the data acquisition is completed for that sample, a new sample is rotated into the beam and its data collection is carried out.

In another embodiment of the invention, samples are mounted on the edge of a rectangular platform. The axis of each sample is perpendicular to the edge of the platform and parallel to the other samples. Samples are changed by translating the platform linearly parallel to the edge on which the samples are mounted, thereby presenting in turn each new sample to the beam. Like the previously described embodiment, the samples may be continually rotated about the longitudinal axis of the capillary in which they are housed, or they may be activated to rotate just prior to, or concurrent with, exposure to the beam. When the data acquisition is completed for that sample a new sample is translated into the beam and its data collection is carried out.

BRIEF DESCRIPTION OF THE FIGURES

For a better understanding of the invention, reference should be made to the following detailed description, taken in conjunction with the accompanying drawings, in which.

Like reference numerals refer to corresponding parts throughout the several views of the drawings.

DETAILED DESCRIPTION OF THE INVENTION

Figure 1:
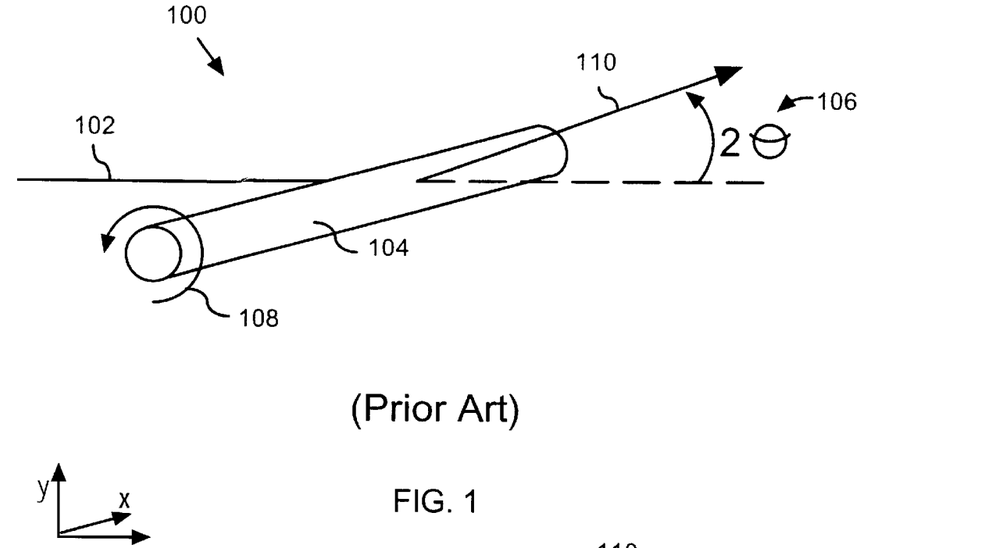
FIG. 1 is a diagrammatic illustration of a prior art capillary geometry X-ray diffraction technique.

FIG. 1 is a diagrammatic illustration of a capillary geometry X-ray diffraction technique 100 known in the art. Typically an X-ray beam 102 is directed at a capillary tube 104 containing a sample to be analyzed. During data aquisition, capillary tube 104 is rotated about its longitudinal axis (rotation illustrated 108) so that a statistical average of the sample can be diffracted and analyzed. The X-ray beam 102 diffracts when encountering the sample, forming a diffracted beam 110. The angle 106 formed between the diffracted beam and the directed beam 102 is typically given the designation 2θ.

Figure 2:
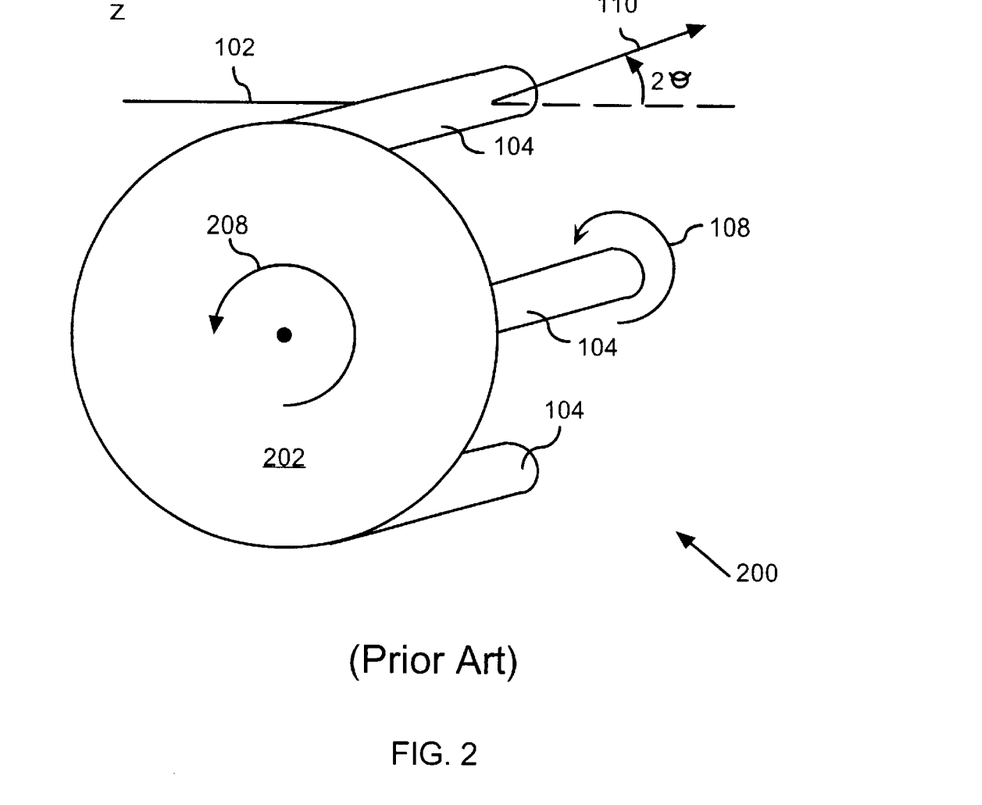
FIG. 2 is a diagrammatic illustration of a prior art sample changer for a capillary geometry X-ray diffractometer.

FIG. 2 is a diagrammatic illustration of a sample changer 200 for a capillary geometry X-ray diffractometer known in the art (sample changer 200 is the same as that disclosed in Creagh et al., supra). A limited number of capillary tubes 104 are located at various positions on a disk 202. The capillary tubes 104 are mounted on the disk 202 such that their longitudinal axes are perpendicular to the surface of the disk. Both the disk 202 and each of the capillary tubes 104 are rotatable as indicated by the arrows 208 and 108, respectively. This device mounts samples onto large goniometer heads (not shown) which permits independent adjustment of their orientations prior to data collection. The rotational axes of the capillary tubes 104 lie parallel to the rotational axis of the disk 202. This arrangement limits the number of samples that can be simultaneously mounted on the disk 202, because if the samples 104 are mounted too close to one another about the periphery of the disk 202, X-ray beam 102 will simultaneously irradiate more than a single sample 104.

For ease of explanation, the following convention will be used to describe the motions of the components. A positive Z direction is along an X-ray beam from the X-ray source. A positive Y direction is upwards in the vertical direction. The positive X direction then defines the right handed coordinate system. Therefore, an observer standing with his back to the radiation source has the positive Z axis in front, the positive X axis to his left and the positive Y axis up. The rotation convention is that a rotation about the X direction (pitch) is called theta (θ), a rotation about the Y direction (yaw) is called phi (φ), and a rotation about the Z direction (roll) is called chi (χ). These axes are illustrated in FIG. 2.

As illustrated in FIG. 2, if we take the origin of the coordinate system to be the sample, then the X axis runs through the longitudinal axis of the capillary of the sample and the X-ray detector's scattering angle, called two theta, rotates about the X axis. The traditional theta angle of the sample rotates about the X axis, and the samples spin about this axis.

Figure 3A:
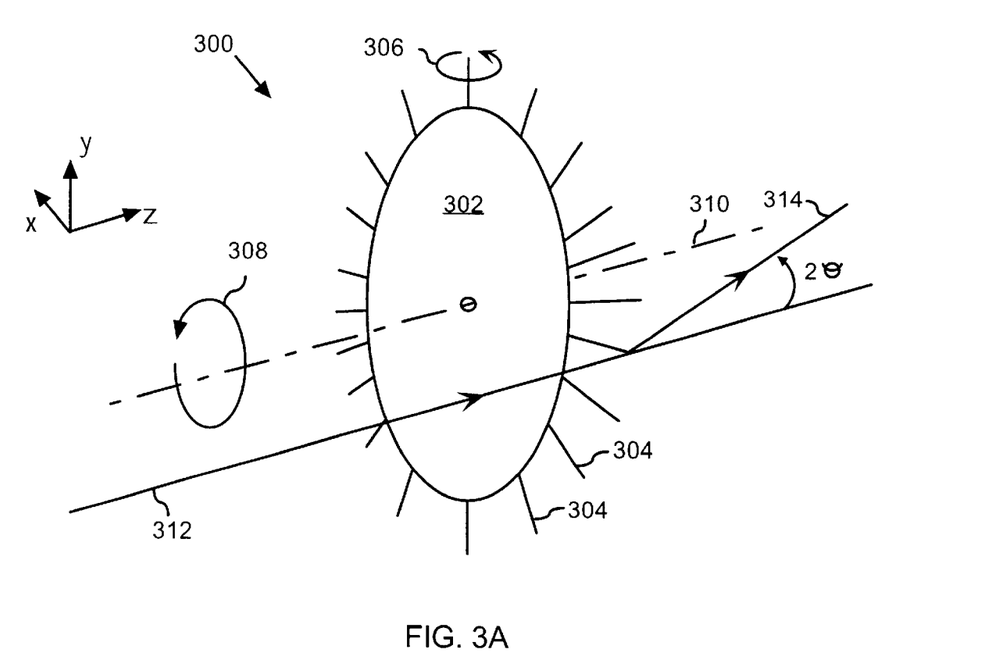
FIG. 3A is a diagrammatic illustration of one embodiment of a sample changer according to the invention.

FIG. 3A is a diagrammatic illustration of one embodiment of a sample changer 300 according to the invention. In this embodiment, a plurality of capillary tubes 304 are disposed about the circumference of a turntable 302. Each capillary 304 contains a sample for analysis (not shown). The longitudinal axis of each capillary extends along a radial which extends from, and lies substantially perpendicular to, a central axis 310 that is perpendicular to the center of turntable 302. Preferably, the plurality of capillaries 304 are disposed equally about turntable 302 (i.e., the angles between the longitudinal axes of all neighboring capillaries are the same). The turntable 302 is rotatable 308 about the central axis 310 (Z axis). The capillary tubes 304 are disposed within rotation devices (not shown, discussed in more detail below), such that they are rotatable 306 about their longitudinal axes. In use, an X-ray beam 312 remains in a single position and the turntable 302 is rotated 308 to sequentially expose each capillary tube 304 to the X-ray beam 312. Diffracted beams 314 are then analyzed for each sample.

Figure 3B:
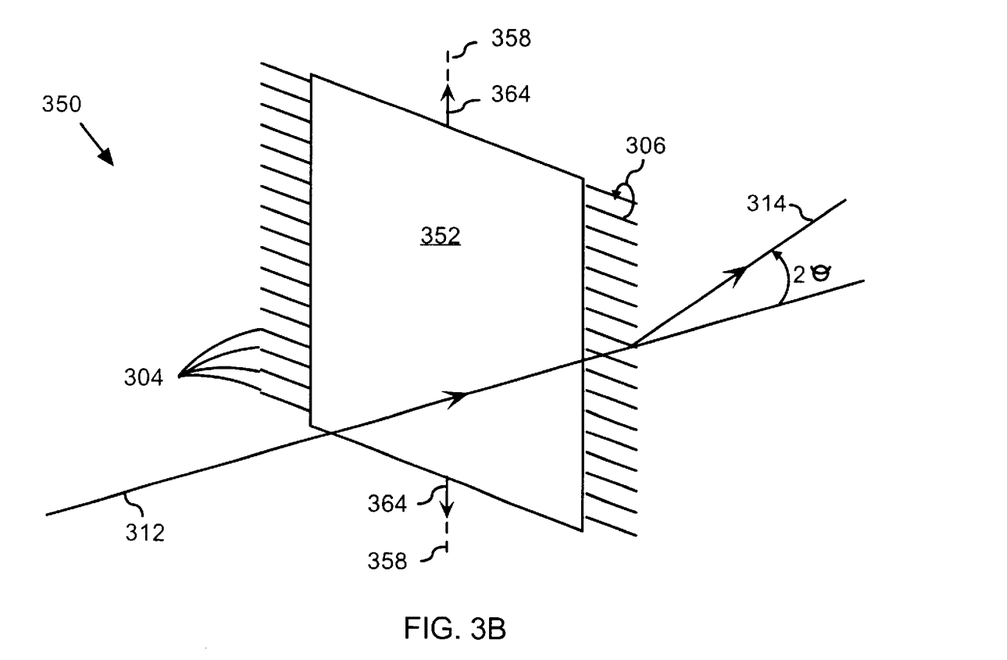
FIG. 3B is a diagrammatic illustration of another embodiment of the invention.

FIG. 3B is a diagrammatic illustration of another embodiment 350 of the invention. Capillary tubes 304 are positioned along the edge of a platform 352 perpendicular to central axis 358 (Y axis). The platform can be translated along the central axis 358 as indicated by the arrows 364. As in the previous embodiment each capillary tube 304 is rotatable 306 about its longitudinal axis. To sequentially expose each capillary tube 304 to an X-ray beam 312, the platform 352 is translated along the central axis 358. Platform 352 is optionally translatable along the X axis or rotatable about central axis 358.

Figure 4A:
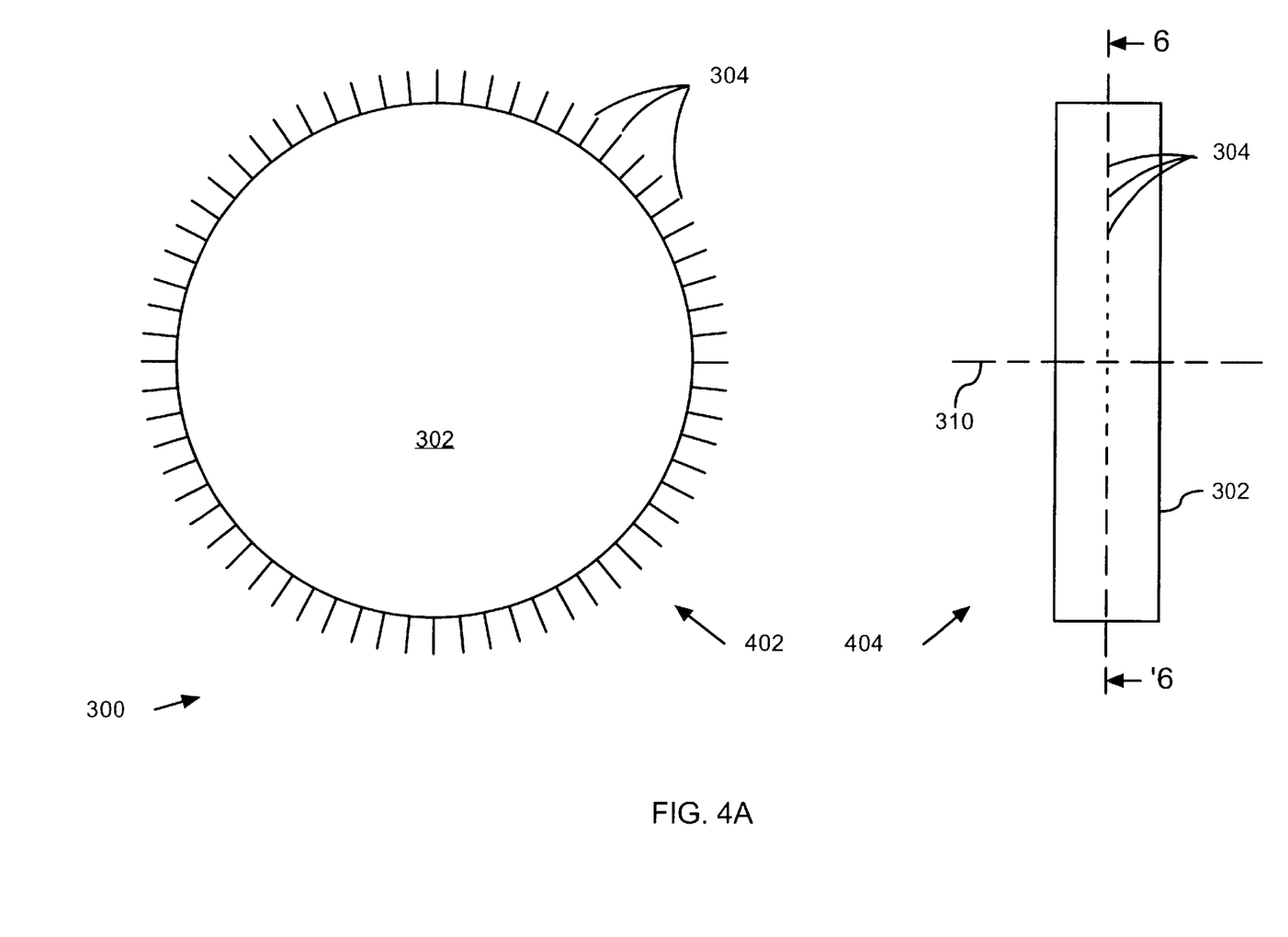
FIG. 4A is an orthographic view of the embodiment shown in FIG. 3A.

FIG. 4A is an orthographic view of the embodiment 300 shown in FIG. 3A. Both a front view 402 and a side view 404 of the turntable 302 are shown. Capillary tubes 304 are disposed about the periphery of turntable 302, which is rotatable about central axis 310 (Z axis).

Figure 4B:
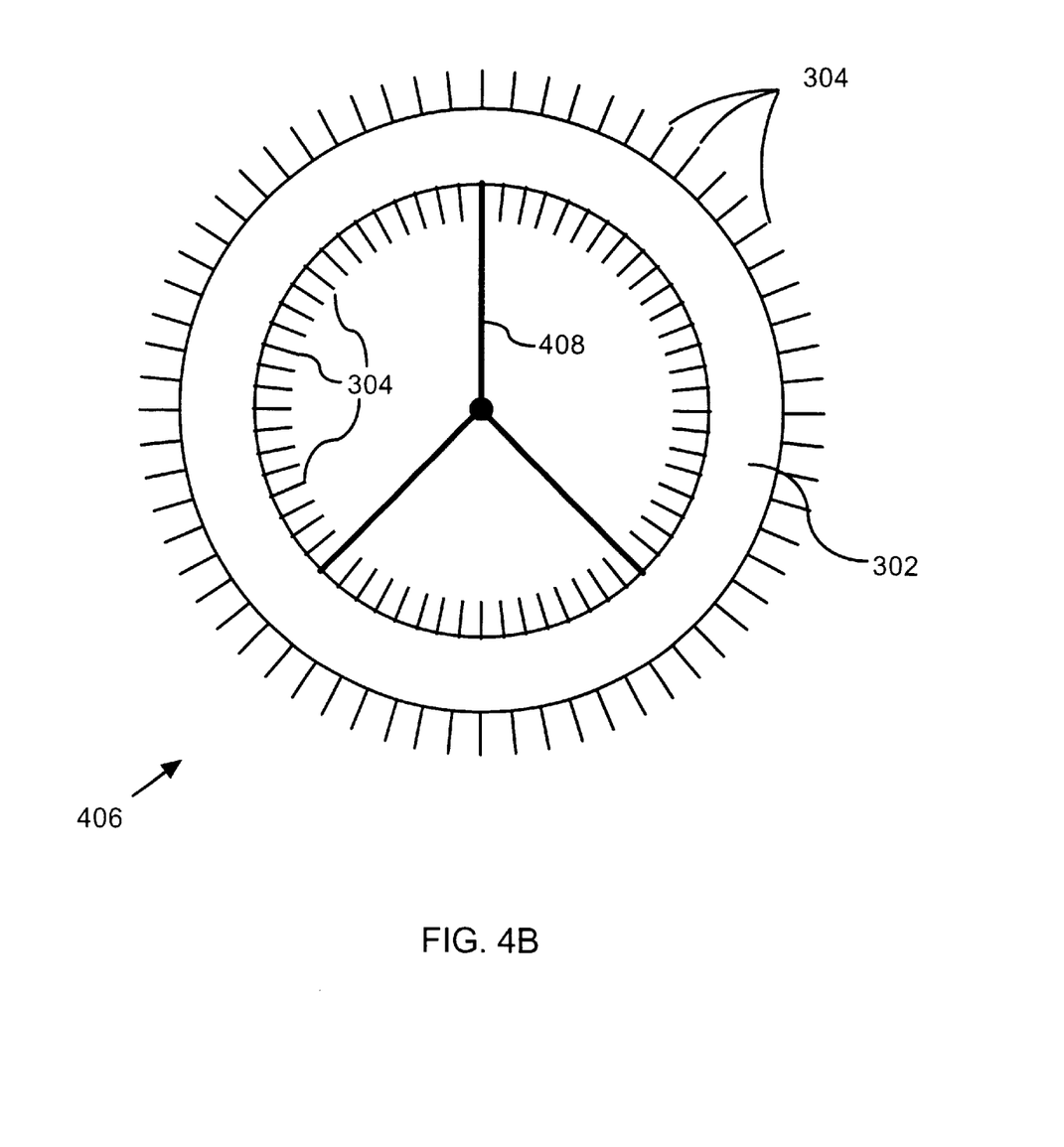
FIG. 4B is a front view of another embodiment of a sample changer according to the invention.

FIG. 4B is a front view of another embodiment 406 of a sample changer according to the invention. In this embodiment, turntable 302 forms a ring with radial spokes 408 emanating from the center of the ring to allow for the rotation of the turntable 302 about the central axis. Capillary tubes 304 extend both outwards from the outer perimeter of the ring and inwards towards the central axis from the inner perimeter of the ring. After analyzing either the outer or inner ring of capillary tubes 304, either the turntable 302 or the X-ray source (not shown) must be translated in line with the next ring of capillary tubes 304 to be analyzed. In this way more capillary tubes 304 may be positioned on a single turntable 302.

Figure 5:
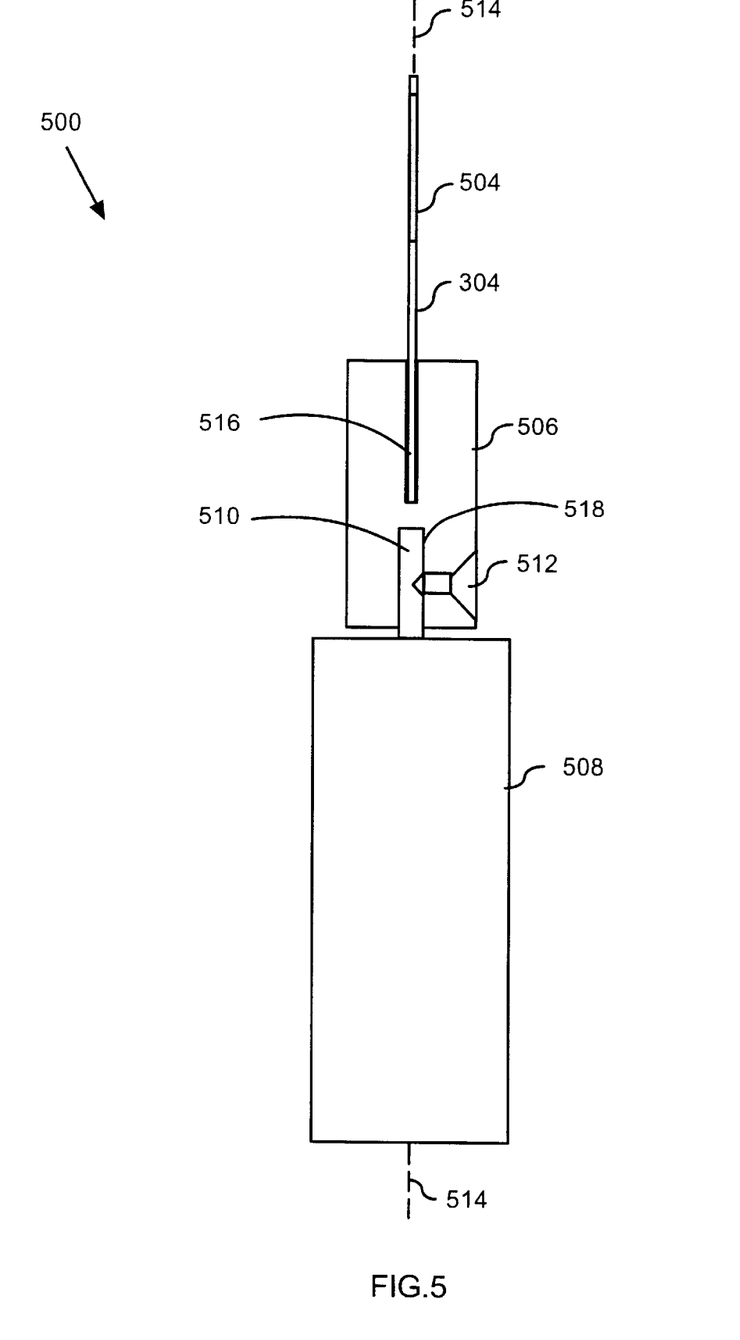
FIG. 5 is a cross sectional view through the center of a rotation device according to the invention, excluding shading lines for clarity.

FIG. 5 is a cross sectional view through the center of a rotation device 500 according to the invention, excluding shading lines for clarity. The rotation device is used to rotate a capillary tube 304 about its longitudinal axis 514. The capillary tube 304 contains a sample 504 which is to be analyzed. The capillary tube 304 is preferably a commercially available capillary tube, such as those supplied by the Charles Supper Company, Natick Mass., U.S.A. The capillary tubes 304 may be as small as 100 micrometers to as much as 5 millimeters in outer diameter. The wall (outer diameter less the inner diameter, of the capillary tube) thickness is preferably 10 micrometers. The capillary tube 304 is preferably made from a X-ray transparent material. The capillary tube 304 is connected to a coupler 506 at a first connector 516. The coupler is preferably cylindrical. First connector 516 is preferably a bore located in the coupler 506 along a rotational axis 514 which coincides with the longitudinal axis of the capillary tube 304. The bore may be a hole drilled in one end of the coupler 506 to receive the capillary tube 304. The hole is drilled precisely along the rotational axis 514 and is sized to match the diameter of the capillary used, whether 0.5 millimeter, 1.0 millimeter, etc., with a snug fit. The capillary tube 304 is securely held in the bore by means of a suitable tacky or adhesive material such as glue, wax, or other deformable or compressible material foam, rubber, etc. The capillary tube 304 may also be held in said bore by any other means, such as by a magnetic force, etc. One skilled in the art will appreciate that any suitable means for connecting the coupler to a capillary tube may be used.

A second connector 518 on the coupler 506 connects the coupler 506 to a shaft 510 of a motor 508. The second connector 518 may also comprise a bore in the coupler 506 and the coupler 506 may be secured to the shaft 510 by any suitable means, such as by means of a set screw 512. The motor 508 is preferably a commercially available DC electric motor such as that available from Micromo, Clearwater Fla., U.S.A. The first and second connecters lie precisely along the rotational axis 514 to guarantee the rotation of the capillary tube 304 about the rotational axis of the motor. One skilled in the art will appreciate that any suitable means for connecting the coupler to the shaft 510 may be used.

In use, motor 508 rotates motor shaft 510 about central axis 514. Since coupler 506 engages both motor shaft 510 and capillary tube 304, coupler 506 and capillary tube 304 also rotate about central axis 514.

The rotation direction and speed of motor 508 can be varied. The objective in rotating motor 508 is to ensure that an appropriate statistical average over all orientations of the crystallites in the sample is achieved. Preferably, an encoder is connected to the motor shaft to count the number of revolutions at each discrete setting of the detector position two theta (2θ). Preferably the shaft rotates the same number of revolutions at each setting of the detector position two theta (2θ).

Figure 6:
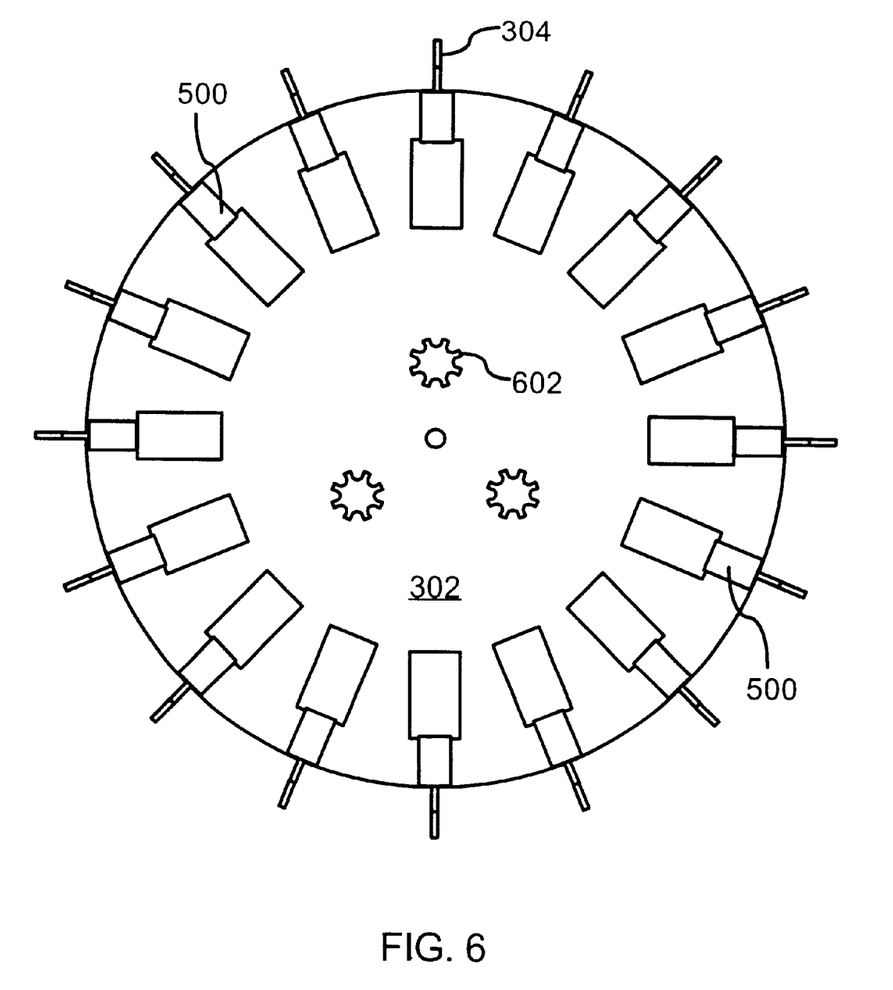
FIG. 6 is a cross sectional view of the embodiment shown in FIG. 4A, taken along line 6'6 of FIG. 4A, excluding shading lines for clarity.

FIG. 6 is a cross sectional view of the turntable 302 shown in FIG. 4A, taken along line 6'6 of FIG. 4A, excluding shading lines for clarity. As can be seen from this sectional view, rotation devices 500 are equally spaced around the perimeter of the turntable 302. The number of rotation devices 500 which can be mounted around the edge of the turntable 302 is only limited by the size of the rotation devices 500 and the diameter of the turntable 302. The rotation devices 500 are mounted with their rotational axes lying along a radial extending substantially perpendicular to a central axis passing through the center of the turntable 302. Holes are preferably drilled around the edge of the turntable 302 to match the diameter of the rotation devices 500 which are slid into the holes. A set screw, or other suitable means, holds the rotation device 500 in place in the turntable 302. By sliding each rotation device 500 into its respective hole to the appropriate depth the sample may be accurately positioned relative to the edge of the disk to guarantee that the capillary tubes 304 are exposed to the X-ray beam when the turntable 302 is rotated. The angle formed between adjacent rotational axes of the rotation devices 500 is preferably about 7.5 degrees. A number of apertures 602 may be provided around the center of the turntable 302 for reproducibly mounting the turntable 302 onto the remainder of the sample changer system, discussed below in relation to FIG. 7. Alternatively, any other suitable means may be used to securely and accurately position the turntable 302 onto the remainder of the sample changer system.

Figure 7:
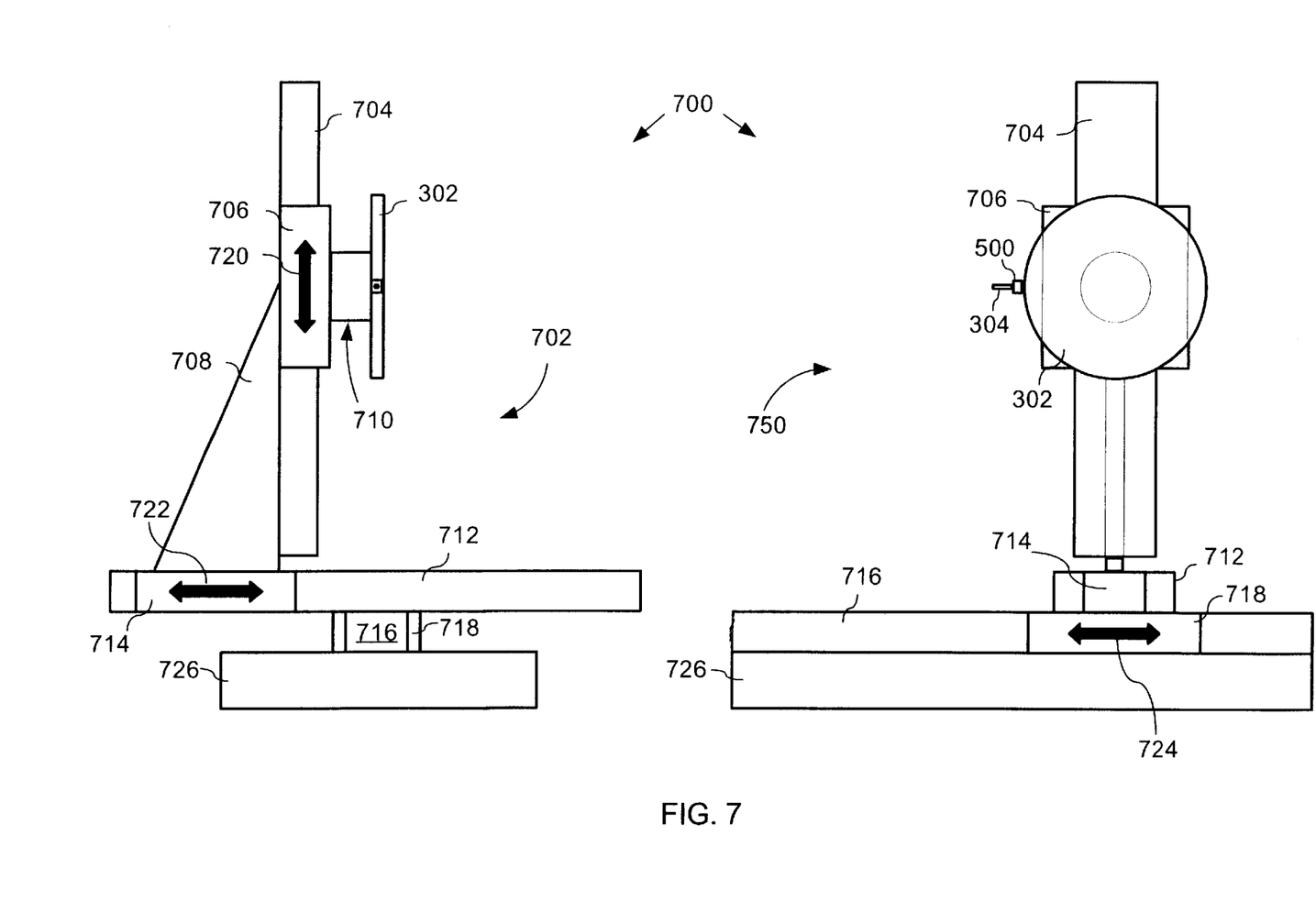
FIG. 7 is an orthographic view of a sample changer system according to the invention.

FIG. 7 is an orthographic view of a sample changer system 700 according to the invention. Sample changer system 700 is shown from both the side 702 and the front 750. Turntable 302 is mounted onto a rotational mechanism 710 which in turn is mounted on a vertical slide 706. Vertical slide 706 is free to move in the vertical direction (Y axis) along a vertical beam 704 as indicated by the arrow 720. The rotational axis of the rotational mechanism 710 coincides with the central axis of the turntable 302. The rotational mechanism 710 is preferably an electric motor. The rotational mechanism 710 rotates the turntable 302 about its central axis, thereby exposing each capillary tube to the X-ray beam.

The vertical beam is connected to a lateral slide 714 by means of a gusset 708. Lateral slide 722 is free to move along a lateral beam 712 as indicated by the arrow 722 (Z axis). The lateral beam 712 is connected to a horizontal slide 718 which is free to move along a horizontal beam 716 as indicated by arrow 7224(X axis). The vertical 706, lateral 714, and horizontal 718 slides allow for the precise positioning and aligning of the turntable 302 and sample to any point in a three dimensional space. The sample changer is finally mounted on a base 726. The sample changer may also be mounted on rotational means which are capable of rotating the sample changer about the three axes.

The axis of rotation of the turntable 302 is parallel to the Z direction, or parallel to the X-ray beam. The turntable's angle can be set accurately enough to bring a new sample into the beam with its axis on the axis of rotation of the an angular 2θ detector within a suitable level of accuracy. This level of accuracy depends upon the diameter of the capillary, and, for example, would be about 20 micrometers for a capillary of 500 micrometers. The preferable radial position is set at a radius of approximately 180 millimeters relative to the axis of rotation of the rotational mechanism 710. A 20 micrometer displacement of the sample at a radius of 180 millimeters corresponds to an angle of about 0.006 degrees. Therefore it is necessary to be able to set the angle of the rotational mechanism 710 to a finer precision than this value. A commercially available rotational mechanism 710 such as the Huber Model 410 available from Blake Industries, Scotch Plains, N.J., is suitable for this purpose. A standard rotary encoder mounted on the turntable is suitable to guarantee that the turntable is set to the correct angle and therefore the sample is in the beam.

The slides 706, 714, and 718 translate the mounting disk in the X, Y, and Z directions respectively. This is necessary to provide an alignment of the sample with respect to the beam. Commercially available linear slides such as Models 3020500XR and 3020600XR available from the Daedal Division of Parker-Hannifin, Irwin, Pa., are suitable for this purpose.

Figure 8:
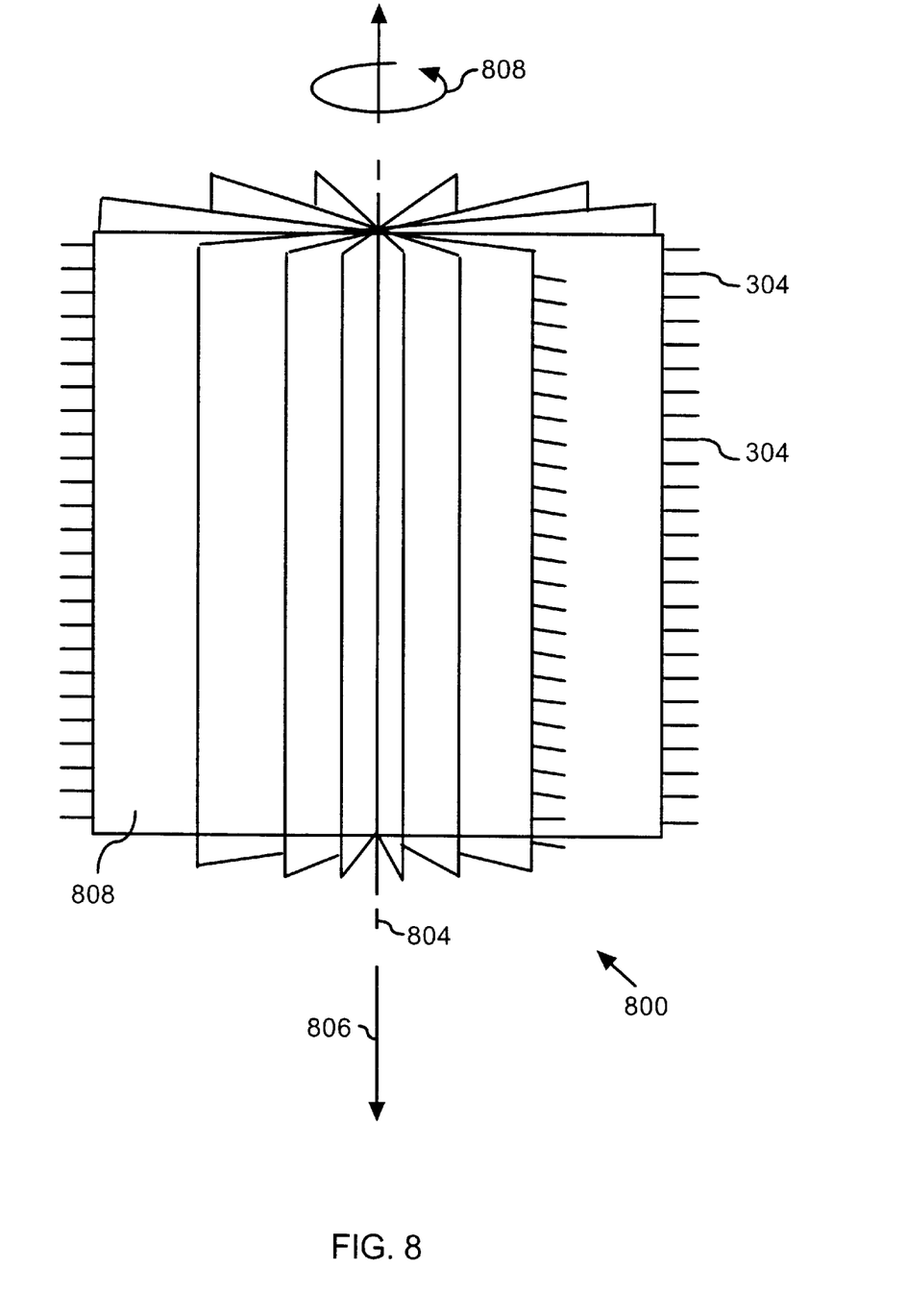
FIG. 8 is a diagrammatic illustration of another embodiment of a sample changer according to the invention.

FIG. 8 is a diagrammatic illustration of another embodiment of the invention. In this embodiment a rotor 800 of platforms, similar to the platform discussed in relation to FIG. 3B, can be rotated 808 about a central axis 804 and translated along the central axis 804. In use a column of capillary tubes 304 mounted on the edge of the platform 808 are analyzed one at a time by moving the platform 808 along axis 804. Thereafter, the rotor 800 is rotated 808 about axis 804 and another column of capillary tubes on another platform is analyzed.

Figure 9:
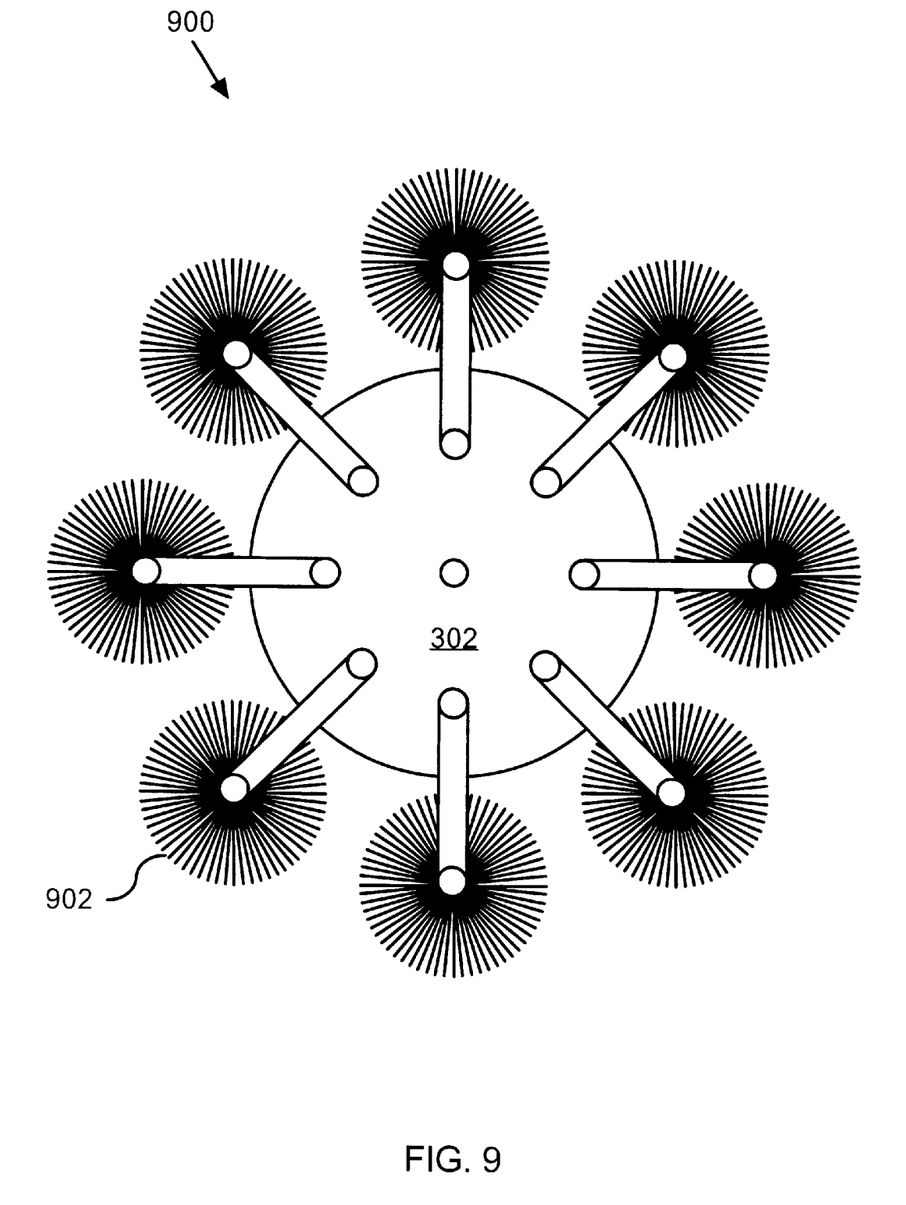
FIG. 9 is a diagrammatic illustration of yet another embodiment of a sample changer according to the invention.

FIG. 9 is a diagrammatic illustration of yet another embodiment of the invention. In this embodiment either multiple turntables or rotors 902 are positioned about a central turntable 302. Each individual turntable or rotor 902 is then analyzed as described in relation to either FIGS. 4–7, or 8 respectively.

The sample changer system is operated in the following manner. A new sample 504 is mounted in a capillary tube 304 of the appropriate diameter. The capillary tube 304 is mounted in the coupler 506 and held in place with a suitable adhesive such as wax or glue. The coupler 506 is mounted onto the shaft of the motor 508. The rotation device 500 is inserted into the turntable 302 and adjusted so that the powder sample is located at a known distance from the edge of the turntable 302. The turntable 302 can be either mounted on the rotational mechanism 710 or on a separate bench while the rotation devices 500 are being mounted onto it. This process is repeated for all motor locations around the edge of the turntable 302, for as many locations as can be accommodated by the diameter of the turntable 302 and the size of the motors. It is convenient to have two different turntables so that one can be used to acquire powder X-ray diffraction data while a second one is being used to mount a series of samples. Mounting each sample so that the powder is a known standard distance from the edge of the mounting disk allows a simple rotation of the turntable to a new sample at the correct position to the beam. Suitable manufacturing of the disks and the turntable with location pins permits a one time alignment of the 706, 714, and 718 slides for any disk installed.

Once a new turntable of samples is mounted on the rotational mechanism 710 then computer controlled data acquisition can be performed. After a data set is acquired on the first sample, a second sample is selected by rotating the turntable to the next sample. The new data set is acquired and once complete a third sample is selected, and so forth. When all of the samples on a disk have been analyzed then a new disk can be installed on the rotational mechanism and a new data collection sequence begun.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof The presently disclosed embodiments are therefore to be considered in all respects as illustrative and not restrictive, the scope of the invention being indicated by the appended claims, and not limited to the foregoing description.

What is claimed is:

1. A sample changer for an X-ray diffractometer, comprising:
    a turntable rotatable about its central axis; and
    a plurality of rotation devices mounted on said turntable, each said rotation device having a rotational axis that lies along a radial extending substantially perpendicular to said central axis, and wherein each said rotation device is independently capable of generating a rotational force about its rotational axis, such that in use each of said rotation devices is capable of independently rotating a sample-holding capillary tube about its longitudinal axis.

2. The sample changer of claim 1, wherein each of said rotation devices further comprises:
    an electric motor with a shaft that rotates about said rotational axis; and
    a coupler that is rotatable about said rotational axis, said coupler comprising:
        a first connector for removably receiving a sample-holding capillary tube, where said first connector is positioned at a distal end of said coupler; and
        a second connector which fastens said coupler to said shaft of said electric motor, where said second connector is positioned at a proximal end of said coupler.

3. The sample changer of claim 2, wherein said first connecter defines a bore in said coupler sized for securely receiving at least a portion of the length of a capillary tube, where said bore extends along said rotational axis.

4. The sample changer of claim 2, wherein said electric motor is a direct current motor.

5. The sample changer of claim 2, wherein said sample changer further includes an encoder which accurately measures rotation of said shaft.

6. The sample changer of claim 1, wherein said rotation devices are spaced about the perimeter of said turntable.

7. The sample changer of claim 1, wherein said sample changer further includes a motor which rotates said turntable.

8. The sample changer of claim 7, wherein said motor is a stepper motor.

9. The sample changer of claim 1, wherein said sample changer further comprises a controller which positions said turntable.

10. The sample changer of claim 9, wherein said sample changer further comprises a regulating mechanism which operates said rotation devices.

11. The sample changer of claim 10, wherein said controller and said regulating mechanism form a single device.

12. The sample changer of claim 10, wherein said controller and said regulating mechanism are computer controlled.

13. A system for X-ray diffraction, comprising:
an X-ray source which emits an X-ray beam;
a detector which detects a diffraction of said X-ray beam; and
a sample changer, comprising:
turntable rotatable about its central axis; and
a plurality of rotation devices mounted on said turntable, each said rotation device having a rotational axis that lies along a radial extending substantially perpendicular to said central axis, and wherein each said rotation device is independently capable of generating a rotational force about its rotational axis.

14. The system of claim 13, wherein each of said rotation devices further comprises:
an electric motor with a shaft that rotates about said rotational axis; and
a coupler rotatable about said rotational axis, comprising
a first connector for removably receiving a sample-holding capillary tube, where said first connector is positioned at a distal end of said coupler; and
a second connector which fastens said coupler to said shaft of said electric motor, where said second connector is positioned at a proximal end of said coupler.

15. The sample changer of claim 14, wherein said second connecter comprises a bore in said coupler sized for securely receiving at least a portion of the length of a capillary tube, where said bore extends along said rotational axis.

16. The system of claim 14 wherein said electric motor is a direct current motor.

17. The system of claim 14, wherein said system further includes an encoder which accurately measures rotation of said shaft.

18. The system of claim 13, wherein said rotation devices are equally spaced about the perimeter of said turntable.

19. The system of claim 13, wherein said system further includes a motor for rotating said turntable.

20. The system of claim 19, wherein said motor is a stepper motor.

21. The system of claim 13, wherein said system further comprises a controller which positions said turntable.

22. The system of claim 21, wherein said system further comprises a regulating mechanism which operates said rotation devices.

23. The system of claim 22, wherein said controller and said regulating mechanism form a single device.

24. The system of claim 22, wherein said controller and said regulating mechanism are computer controlled.

25. The system of claim 22, wherein said X-ray beam is chosen for properties selected from a group consisting of:
collimation, spot size, energy resolution, and intensity.

26. A sample changer for an X-ray diffractometer, comprising:
a platform translatable along a central axis, where said platform has a substantially planar surface; and
a plurality of rotation devices mounted on said platform, where each of said rotation devices generates a rotational force about its rotational axis which lies along a radial extending substantially perpendicular to said central axis and parallel to said planar surface,
and where each of said rotation devices is configured to independently rotate a sample-holding capillary tube about its longitudinal axis that is parallel to said planar surface.

27. The sample changer of claim 26, wherein each of said rotation devices further comprises:
an electric motor with a shaft that rotates about said rotational axis; and
a coupler rotatable about said rotational axis, said coupler comprising:
a first connector for removably receiving a sample-holding capillary tube, where said first connector is positioned at a distal end of said coupler; and
a second connector which fastens said coupler to said shaft of said electric motor, where said second connector is positioned at a proximal end of said coupler.

28. The sample changer of claim 27, wherein said second connecter comprises a bore in said coupler sized for securely receiving at least a portion of the length of a capillary tube, where said bore extends along said rotational axis.

29. The sample changer of claim 27, wherein said electric motor is a direct current motor.

30. The sample changer of claim 27, wherein said sample changer further includes an encoder which accurately measures rotation of said shaft.

31. The sample changer of claim 26, wherein said rotation devices are spaced along the edge of said platform.

32. The sample changer of claim 26, wherein said sample changer further includes a mechanism which translates said platform.

33. The sample changer of claim 26, wherein said sample changer further comprises a controller which positions said platform.

34. The sample changer of claim 33, wherein said sample changer further comprises a regulating mechanism which operates said rotation devices.

35. The sample changer of claim 34, wherein said controller and said regulating mechanism form a single device.

36. The sample changer of claim 34, wherein said controller and said regulating mechanism are computer controlled.

* * * * *